United States Patent
Goto et al.

(10) Patent No.: US 8,296,081 B2
(45) Date of Patent: Oct. 23, 2012

(54) METHOD FOR PROVISION AND UTILIZATION OF MATERIAL INFORMATION REGARDING STEEL SHEET FOR SHIPPING

(75) Inventors: Koichi Goto, Tokyo (JP); Tadaaki Shikama, Tokyo (JP); Ikuo Oonishi, Tokyo (JP)

(73) Assignee: Nippon Steel Corporation, Tokyo (JP)

( * ) Notice: Subject to any disclaimer, the term of this patent is extended or adjusted under 35 U.S.C. 154(b) by 336 days.

(21) Appl. No.: 12/733,072

(22) PCT Filed: Aug. 15, 2008

(86) PCT No.: PCT/JP2008/064957
§ 371 (c)(1),
(2), (4) Date: Feb. 4, 2010

(87) PCT Pub. No.: WO2009/025344
PCT Pub. Date: Feb. 26, 2009

(65) Prior Publication Data
US 2010/0241365 A1    Sep. 23, 2010

(30) Foreign Application Priority Data
Aug. 17, 2007   (JP) ................................. 2007-212762

(51) Int. Cl.
*G01B 3/00* (2006.01)
*G01B 5/28* (2006.01)
*G01B 5/30* (2006.01)
*C21D 11/00* (2006.01)
*C21D 1/55* (2006.01)

(52) U.S. Cl. ................ 702/33; 702/34; 702/35; 72/8.1; 148/508

(58) Field of Classification Search .................... 702/33, 702/34, 35; 72/8.1; 148/508
See application file for complete search history.

(56) References Cited

U.S. PATENT DOCUMENTS

| | | | | |
|---|---|---|---|---|
| 5,054,302 A | * | 10/1991 | Yamashita et al. | 72/8.4 |
| 6,269,668 B1 | * | 8/2001 | Shiraishi et al. | 72/8.6 |
| 2004/0054660 A1 | * | 3/2004 | McCormick | 707/3 |

FOREIGN PATENT DOCUMENTS

JP          5-142126          6/1993
(Continued)

OTHER PUBLICATIONS

International Search Report dated Nov. 18, 2008 issued in corresponding PCT Application No. PCT/JP2008/064957.

*Primary Examiner* — Janet Suglo
(74) *Attorney, Agent, or Firm* — Kenyon & Kenyon LLP

(57) ABSTRACT

The present invention provides a method for obtaining material information regarding steel sheet for shipping over the entire length of the steel sheet for shipping without spending too much time and effort, providing detailed material information in large volumes to a user through a computer and network, and having the user utilize the same. Specifically, it estimates the mechanical properties of temper rolled steel sheet based on the actual rolling data in a skinpass mill installed at the exit side of the continuous annealing line or galvanization facility and provides the estimated mechanical properties through the host computer and network to the user of the steel sheet. The user can use the estimated material information so as to remove the parts defective in mechanical properties or change the press forming conditions of the steel sheet. Further, the user can feed back information to the steel sheet manufacturer.

9 Claims, 10 Drawing Sheets

FOREIGN PATENT DOCUMENTS

| | | |
|---|---|---|
| JP | 5212406 A * | 8/1993 |
| JP | 06-010055 | 1/1994 |
| JP | 2003-215052 | 7/2003 |
| JP | 2004-157113 | 6/2004 |
| JP | 2004-277835 | 10/2004 |
| JP | 2005-074448 | 3/2005 |

* cited by examiner

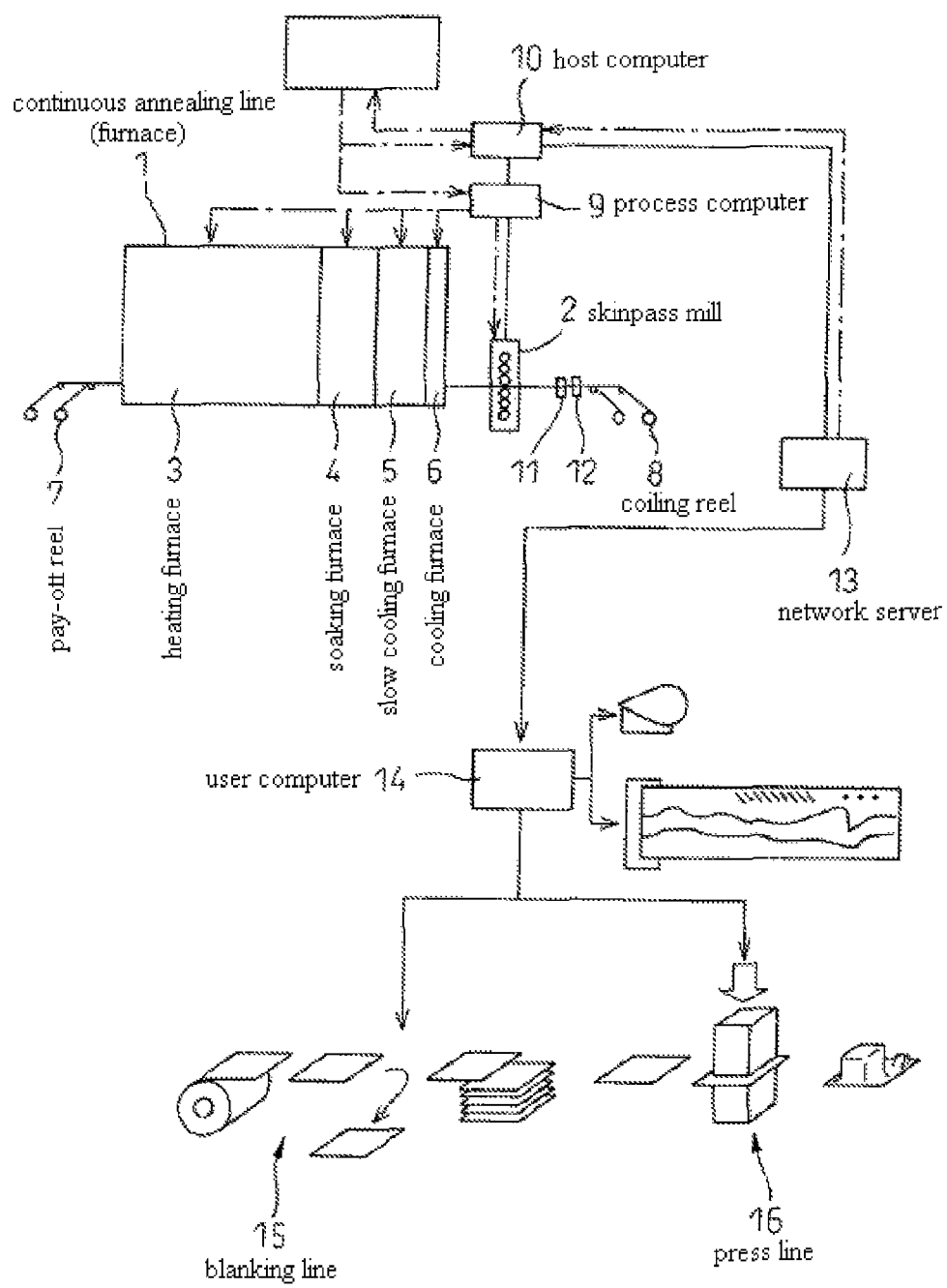

METHOD FOR PROVISION AND UTILIZATION OF MATERIAL INFORMATION REGARDING STEEL SHEET FOR SHIPPING

This application is a national stage application of International Application No. PCT/JP2008/064957, filed 15 Aug. 2008, which claims priority to Japanese Application No. 2007-212762, filed 17 Aug. 2007, which is incorporated by reference in its entirety.

TECHNICAL FIELD

The present invention relates to a method of provision of material information regarding steel sheet for shipping and a method of utilization of the same. Specifically, it relates to a method of estimating mechanical properties of steel sheet from actual rolling data at a skinpass mill (SPM) in the rolling of steel sheet and providing the estimated results to a user through a computer and network and to a method of utilization of that information.

BACKGROUND ART

Steel manufacturers have been sampling parts of the steel sheet for shipping out and provided the results of tensile tests to users as material information. At the same time, defects and other quality information, for example as described in Japanese Patent Publication (A) No. 2003-215052, is being supplied as defect inspection results together with images and positional information in the longitudinal direction of the steel sheet to users as electronic information through computers.

In the above way, usually the tensile tests of steel sheet have been performed by sampling parts of the steel sheet shipped out. The tensile tests are run off line, so only the mechanical properties data of the sampled parts of the shipped out steel sheet can be obtained. If trying to obtain detailed material information on the shipped out steel sheet, it would be necessary to take a large number of samples for tensile tests. For this reason, the steel sheet would have to be finely divided and, accordingly, it would no longer possible to meet the predetermined shipment weights. Further, even if taking a large number of steel sheet samples, tremendous time and effort would be required for the tensile tests. This would not be practical.

On the other hand, quality information like surface defects is detected by surface defect detection devices installed on the steel sheet production lines. The data is compiled by computer and can be provided to the users through a network.

However, for the yield strength, tensile strength, and other mechanical properties, the only means for measuring the mechanical properties is to take steel sheet samples and test them for mechanical properties. It is impossible to provide the users with these mechanical properties for entire lengths.

Further, in some places, r-value detection devices using non-destructive, magnetic flux measurement have been installed on the steel sheet production lines, but adjustment is required for each type of product such as mild steel sheet or high-tensile steel sheet and only specific mechanical properties could be measured, so these were not universally applicable.

DISCLOSURE OF THE INVENTION

A purpose of the present invention is to solve the above problems and provide a method for obtaining material information for an entire length of steel sheet shipped out with less time and effort, providing that detailed material information to users over a computer and network, and enabling the users to utilize said material information.

Furthermore, another purpose of the present invention is to provide a method of utilization of material information of shipped out steel sheet feeding back information from users regarding the steel sheet mechanical properties and working conditions and positions of the same to the steel sheet manufacturer and thereby improving the productivity and quality of the steel sheet production line.

The inventors engaged in intensive studies to solve the above problems and as a result took note of the fact that it is possible to precisely estimate the mechanical properties of steel sheet (material estimation) based on actual rolling data in a skinpass mill arranged at an exit side of a continuous annealing line or galvanization facility and discovered that if effectively using the estimated mechanical properties, it is possible to provide a steel sheet user with more detailed material information than the present. Further, the invention has as its gist as following:

(1) A method of provision of material information regarding steel sheet for shipping by use of estimation method of mechanical properties of temper rolled steel sheet characterized by
  estimating the mechanical properties of temper rolled steel sheet based on actual rolling data in a skinpass mill installed at an exit side of a continuous annealing line or galvanization facility and providing the estimated mechanical properties to a user of said steel sheet through a computer and network.

(2) A method of provision of material information regarding steel sheet for shipping by use of estimation method of mechanical properties of temper rolled steel sheet as set forth in (1) characterized by
  measuring or acquiring from a host computer the values of elongation rate, tension, and rolling load of steel sheet in a skinpass mill installed at an exit side of a continuous annealing line or galvanization facility and the sheet thickness and sheet width of said steel sheet, using these values to estimate the mechanical properties of temper rolled steel sheet, and providing the estimated mechanical properties to a user of said steel sheet through a computer and network.

(3) A method of provision of material information regarding steel sheet for shipping by use of estimation method of mechanical properties of temper rolled steel sheet as set forth in (1) or (2) characterized by
  continuously measuring or acquiring from a host computer said values of elongation rate, tension, and rolling load of steel sheet and the sheet thickness and sheet width of said steel sheet over the entire length of said steel sheet, using these values to estimate the mechanical properties of temper rolled steel sheet, and providing the estimated mechanical properties to a user of said steel sheet through a computer and network.

(4) A method of provision of material information regarding steel sheet for shipping by use of estimation method of mechanical properties of temper rolled steel sheet as set forth in any one of (1) to (3) characterized by
  estimating the mechanical properties of temper rolled steel sheet using a estimation formula for calculating a yield point of said steel sheet from values of the elongation rate, tension, and rolling load of said steel sheet in a skinpass mill and a sheet thickness and sheet width of said steel sheet.

(5) A method of utilization of material information regarding steel sheet for shipping by use of estimation method of mechanical properties of temper rolled steel sheet characterized by using material information obtained by a method of provision of material information of steel sheet by use of estimation method of mechanical properties of temper rolled steel sheet as set forth in any one of (1) to (4) so as to remove defective parts of said steel sheet in mechanical properties.

(6) A method of utilization of material information regarding steel sheet for shipping by use of estimation method of mechanical properties of temper rolled steel sheet characterized by using material information obtained by a method of provision of material information of steel sheet by use of estimation method of mechanical properties of temper rolled steel sheet as set forth in any one of (1) to (4) so as to change press forming conditions of said steel sheet.

(7) A method of utilization of material information regarding steel sheet for shipping by use of estimation method of mechanical properties of temper rolled steel sheet as set forth in (5) characterized by feeding back material information and positioning information of removed part of steel sheet by a user and one or both of material information or press forming conditions to the manufacturer of said steel sheet through a computer and network.

(8) A method of utilization of material information regarding steel sheet for shipping by use of estimation method of mechanical properties of temper rolled steel sheet as set forth in (6) characterized by feeding back on material information and positioning information of steel sheet obtained by a user changing press forming conditions of the steel sheet to the manufacturer of said steel sheet through a computer and network.

BRIEF DESCRIPTION OF THE DRAWINGS

FIG. 10 is a schematic view showing an embodiment of the present invention.

BEST MODE FOR CARRYING OUT THE INVENTION

Figure 1:
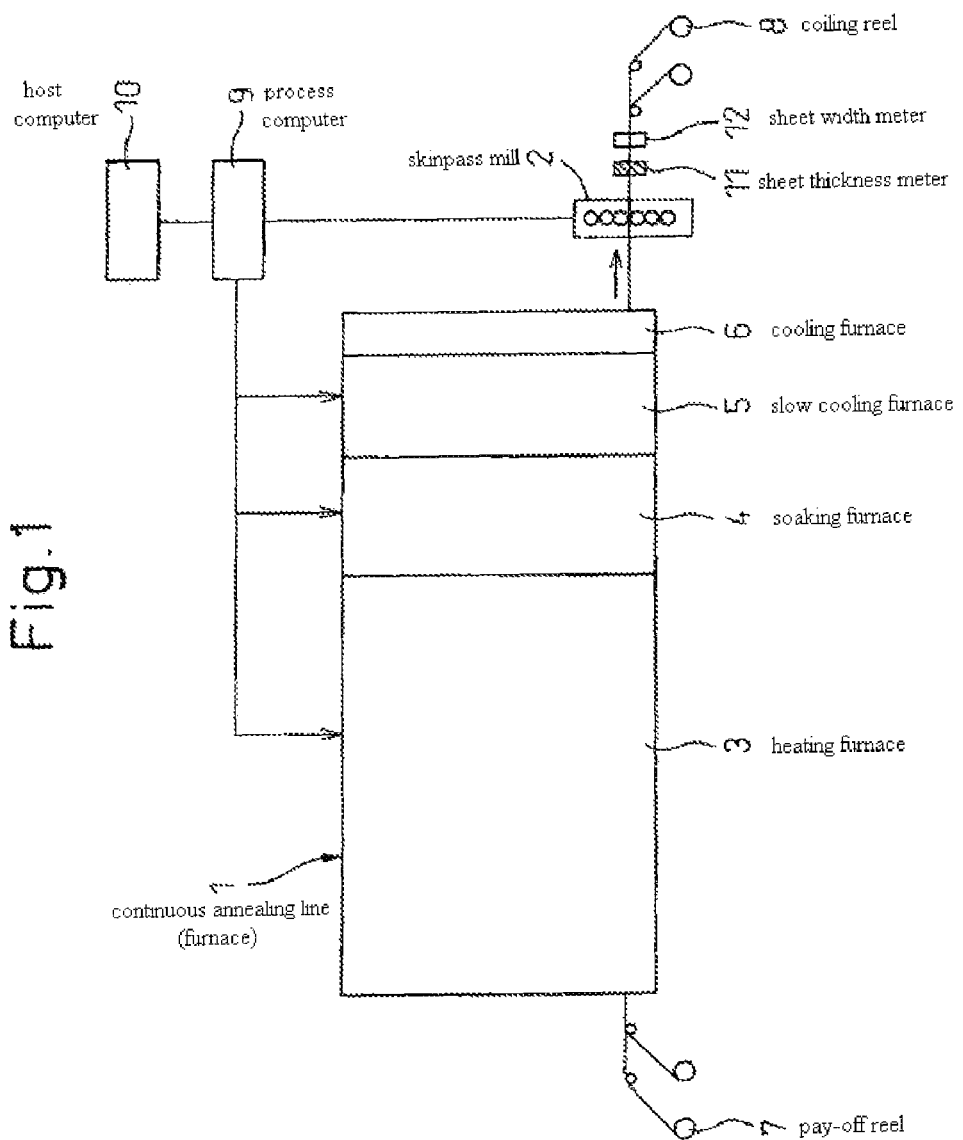
FIG. 1 is a schematic view of a continuous annealing line.

One major feature of the present invention is the estimation of the mechanical properties of temper rolled steel sheet based on actual rolling data in a skinpass mill installed at an exit side of a continuous annealing line or galvanization facility and provision of the estimated mechanical properties data as mechanical properties characteristic values of shipped out steel sheet through a host computer and network to a user of the steel sheet. Of course, the voucher of the shipped out steel sheet continues as usual to have the results of tensile tests performed using samples of the steel sheet taken from part of the shipped out steel sheet attached to it.

However, in the present invention, a big feature is the point that while estimated values, good precision mechanical properties characteristic values can be provided to the user even for parts other than the steel sheet sample taken. Specifically, the mechanical properties of the temper rolled steel sheet are estimated based on the actual rolling data in a skinpass mill installed at an exit side of a continuous annealing line or galvanization facility.

Further, preferably it is also possible to estimate a yield point (YP) of a temper rolled steel sheet from actual rolling data in a skinpass mill and precisely estimate a tensile strength (TS) from the estimated yield point (YP) in accordance with need.

First, below, regarding the method of estimation of mechanical properties, embodiments of the present invention will be shown while referring to the drawings using the example of a skinpass mill installed at the exit side of a continuous annealing line or an exit side of a galvanization facility.

Further, in the case of a galvanization facility, it may be considered that there is a galvanization facility between the annealing furnace and the skinpass mill. Below, the explanation will be given with reference to the example of a continuous annealing line.

FIG. 1 is a view schematically showing a continuous annealing line of steel sheet, wherein 1 is a continuous annealing furnace, and 2 is a skinpass mill installed at its exit side. The continuous annealing furnace 1 is roughly divided into a heating furnace 3, primary soaking furnace 4, secondary soaking furnace 5, and cooling furnace 6. Steel sheet paid off from pay-off reel 7 successively runs through these heating furnace 3, primary soaking furnace 4, and secondary soaking furnace 5 during which the steel sheet is heated to a temperature suitable for its mechanical properties and annealed, then is quenched and cooled from the outlet temperature of the secondary soaking furnace 5 in the cooling furnace 6, is temper rolled at the skinpass mill 2, then is coiled up by a coiling reel 8.

Note that between the cooling furnace 6 and the skinpass mill 2, an overaging furnace or cooling furnace or a hot dipping facility, an alloying facility, an electroplating facility, or other surface treatment facility for producing surface treated steel sheet may be provided. The above configuration is no different from the conventional process. The sheet temperature at each part is highly controlled as explained above.

In the skinpass mill 2, the sheet is temper rolled by light rolling. In the present invention, the rolling load (SPM rolling load), tension (SPM tension), and elongation rate (SPM elongation rate) in the skinpass mill 2 are continuously sensed and then the mechanical properties are estimated In particular, to accurately estimate the mechanical properties of steel sheet having a 780 MPa or higher tensile strength (so-called high-tensile steel sheet), it is preferable to estimate the mechanical properties taking into consideration not only the SPM tension and SPM elongation rate, but also the SPM rolling load.

Figure 2:
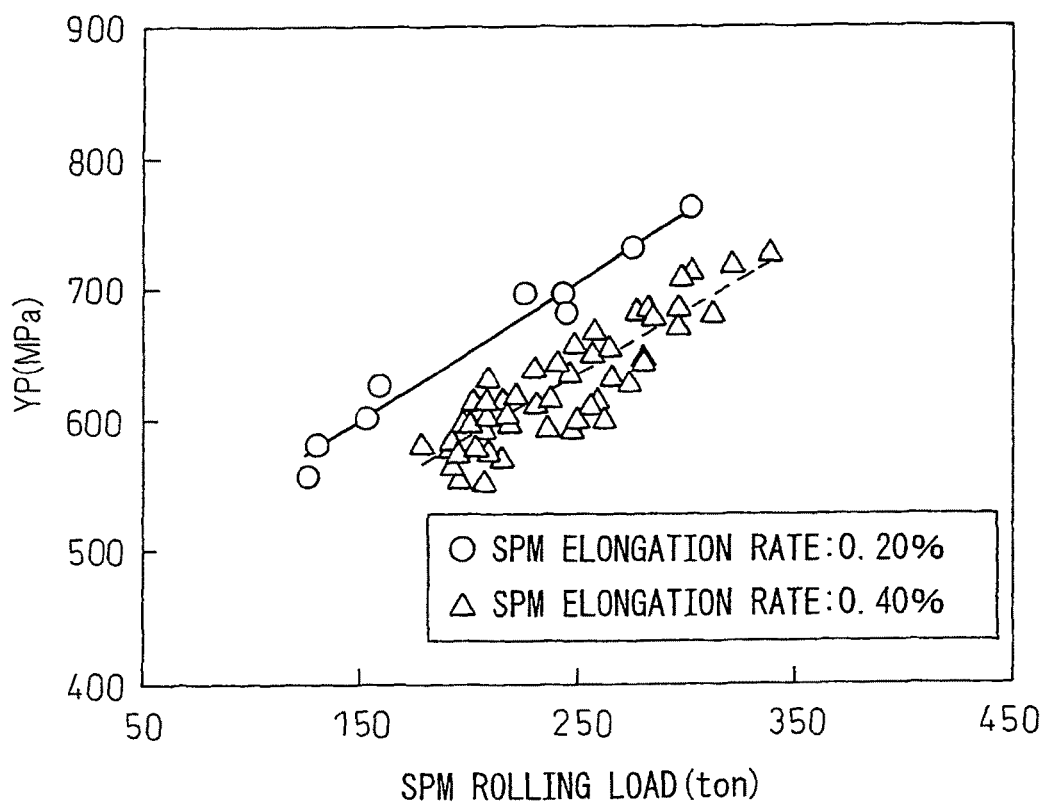
FIG. 2 is a graph showing the correlation between a rolling load and YP.
Figure 3:
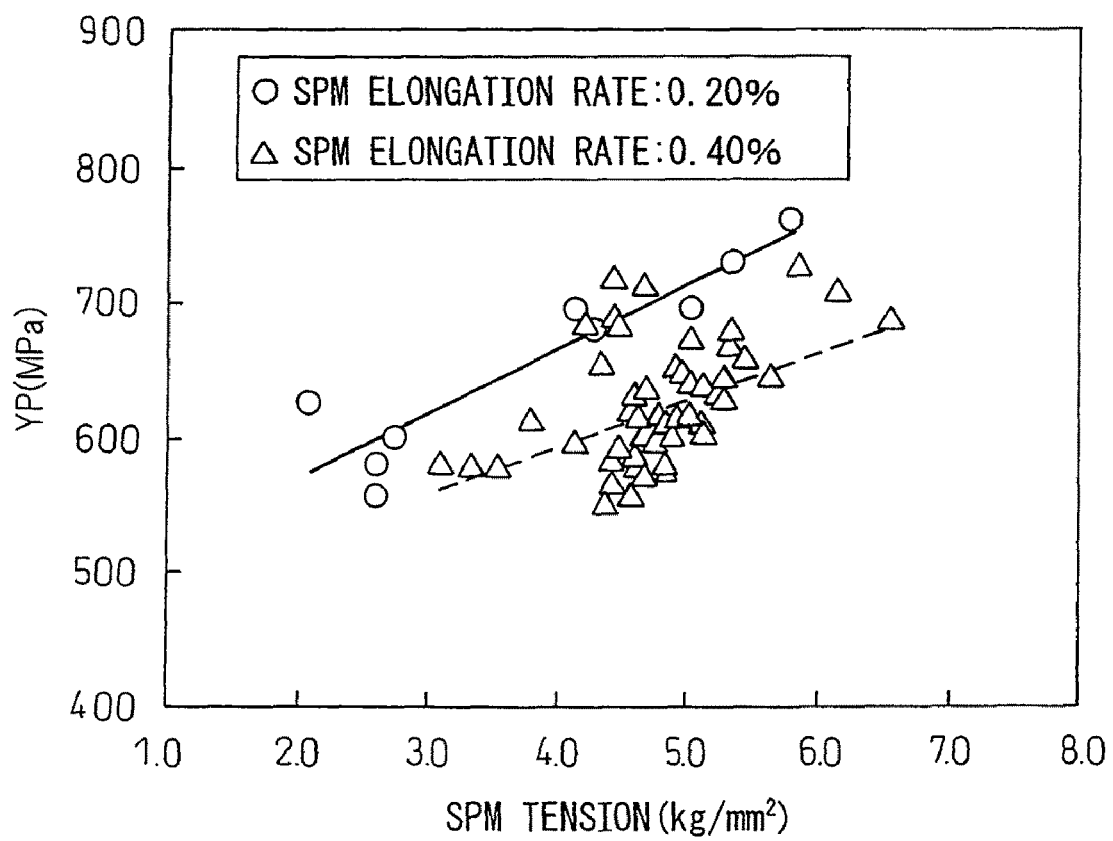
FIG. 3 is a graph showing the correlation between a rolling tension and YP.

More preferably, the present invention provides to continuously sense the SPM rolling load, SPM tension, and SPM elongation rate in the skinpass mill 2, to estimate the yield point (YP) of the temper rolled steel sheet, and the tensile strength (TS) from the estimated value of the yield point (YP). FIG. 2 and FIG. 3 show the correlation between the rolling load in high-tensile steel sheet having a 780 MPa or more tensile strength and high-tensile steel sheet with the yield point. Further, FIG. 4 and FIG. 5 show the correlation with the rolling load and tensile strength at said high-tensile steel sheet.

Figure 4:
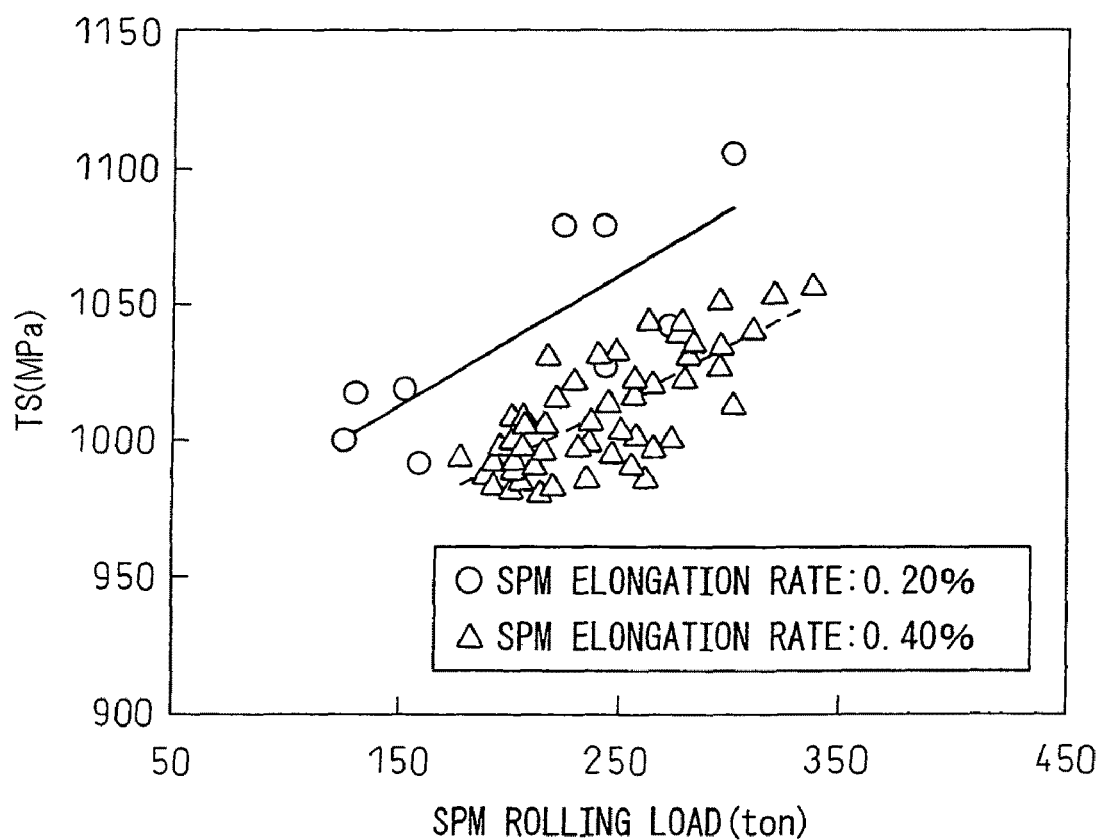
FIG. 4 is a graph showing the correlation between a rolling load and TS.
Figure 5:
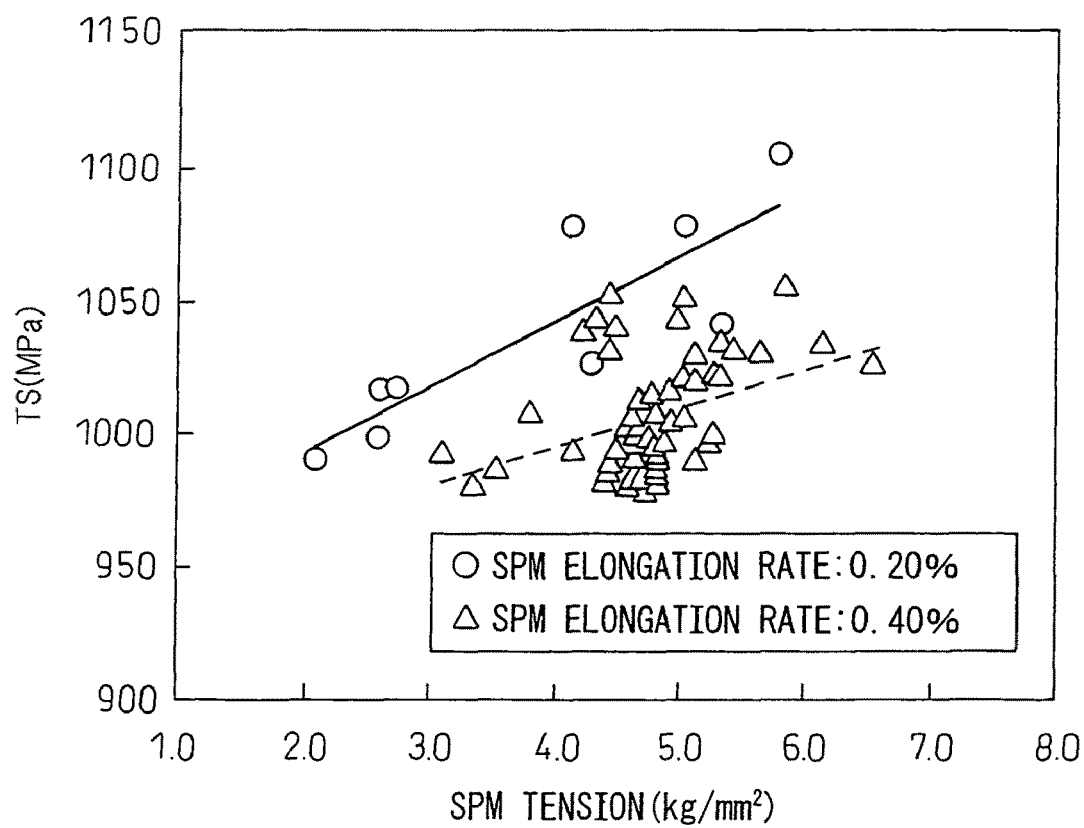
FIG. 5 is a graph showing the correlation between a rolling tension and TS.

That is, according to the actual rolling data, as shown in FIG. 2 and FIG. 3, if the SPM elongation rate is the same, if the SPM rolling load and SPM tension increase, the yield point (YP) of the temper rolled steel sheet will increase and, as shown in FIG. 4 and FIG. 5, the tensile strength (TS) will also increase.

Further, even if the SPM rolling load or the SPM tension is constant, with a lower SPM elongation rate, the yield point (YP) and tensile strength (TS) become greater. Due to this, it is learned that there is a strong correlation among the SPM rolling load, SPM tension, SPM elongation rate, and mechanical properties (YP, TS) of temper rolled steel sheet.

Therefore, based on actual past operating data, we prepared a formula for estimating the mechanical properties of temper rolled steel sheet. We included in the Roberts formula known as the theoretical formula for temper rolling numerous impact factors such as the mechanical properties (YP, TS), SPM elongation rate, SPM tension, friction coefficient, thickness, rolling speed, roll diameter, etc. By precisely using these factors, highly precise estimation of mechanical properties becomes possible. As an example of the present invention, we prepared the following formula. As impact factors, we used the elongation rate (%) of the skinpass mill, the tension (MPa) of the skinpass mill, the sheet thickness (mm) of the steel sheet, and the linear load (ton/m) calculated from the SPM rolling load of the skinpass mill and the sheet width of the steel sheet:

$$YP=a*SPM \text{ elongation rate } (\%)+b*(\text{average tension MPa})+c*(\text{sheet thickness mm of steel sheet}*\text{line load ton/m})+d$$

In this formula, YP is the yield point with a unit of MPa, while the linear load is the value of the SPM rolling load divided by the width of the steel sheet. The coefficients included in this formula are determined by multiple linear regression analysis. The specific values of a, b, c, and d in said formula and the form of the formula are determined by the characteristics of the individual lines and the strength of the steel sheet being processed and are not limited to the above.

Incidentally, if applying temper rolling with a fixed rolling load as often practiced with mild steel sheet to 780 MPa or greater high-tensile steel sheet, due to the high tensile strength of the steel sheet, it becomes temper rolling with an excessive rolling load and tension balance close to the limit of the specifications of the facilities. The rolling itself becomes extremely unstable. In the worst case, trouble such as sheet breakage may even be caused.

Note that, regarding said SPM tension, in actual operation, there is tension at the entry side and exit side of the skinpass mill, but the two are in a generally proportional relationship. For the value used for estimating the mechanical properties, either the entry side or exit side may be used, but it is preferable to use an average of the two. Regarding the sheet thickness and sheet width of the steel sheet, it is possible to measure either the value at the entry side or the value at the exit side of the skinpass mill or obtain and use it from the host computer. Preferably, the value at the exit side of the skinpass mill is used due to the influence of the elongation of the steel sheet in the annealing furnace.

In estimating the mechanical properties of temper rolled steel sheet, in particular high-tensile steel sheet having a TS of 780 MPa or more, when employing the SPM rolling load of the skinpass mill as the impact factor, the TS can be estimated extremely accurately due to the following reason, it is presumed.

In general mild steel sheet, the steel sheet is relatively soft, and the skinpass mill has extra leeway in the SPM rolling load and SPM tension capabilities for such mild steel sheet, so when either of the rolling load or tension fluctuates, the rolling control system of the skinpass mill can control the tension or the rolling load to keep the elongation rate constant. For instance, when the rolling load fluctuates, the control system controls the tension to keep the elongation rate being constant. In that case, just the tension can be used as the impact factor.

However, with high-tensile steel sheet having a TS of 780 MPa or more, the skinpass mill does not have extra capacity in terms of the SPM rolling load and SPM tension capabilities for such high-tensile steel sheet and often operates at the limits of these capabilities. If either of the rolling load or tension fluctuates, each other will sometimes not be able to absorb it. With just one of the rolling load or tension, the estimation precision cannot be raised. It is believed necessary to estimate mechanical properties comprehensively from the tension, rolling load (linear load calculated by above formula), and elongation rate.

Further, as impact factors for estimating the mechanical properties, it is preferable to consider at least one of the work roll diameter of the skinpass mill, the friction coefficient between the work roll of the skinpass mill and steel sheet, and the rolling speed of the skinpass mill.

When the roll diameter of the skinpass mill work and the friction coefficient between the work roll of the skinpass mill and steel sheet are hard to determine during rolling of the steel sheet, it is also possible to use values measured or determined in advance. For the rolling speed at the skinpass mill, either of the value at the entry side or the value at the exit side of the skinpass mill may be used.

Figure 6:
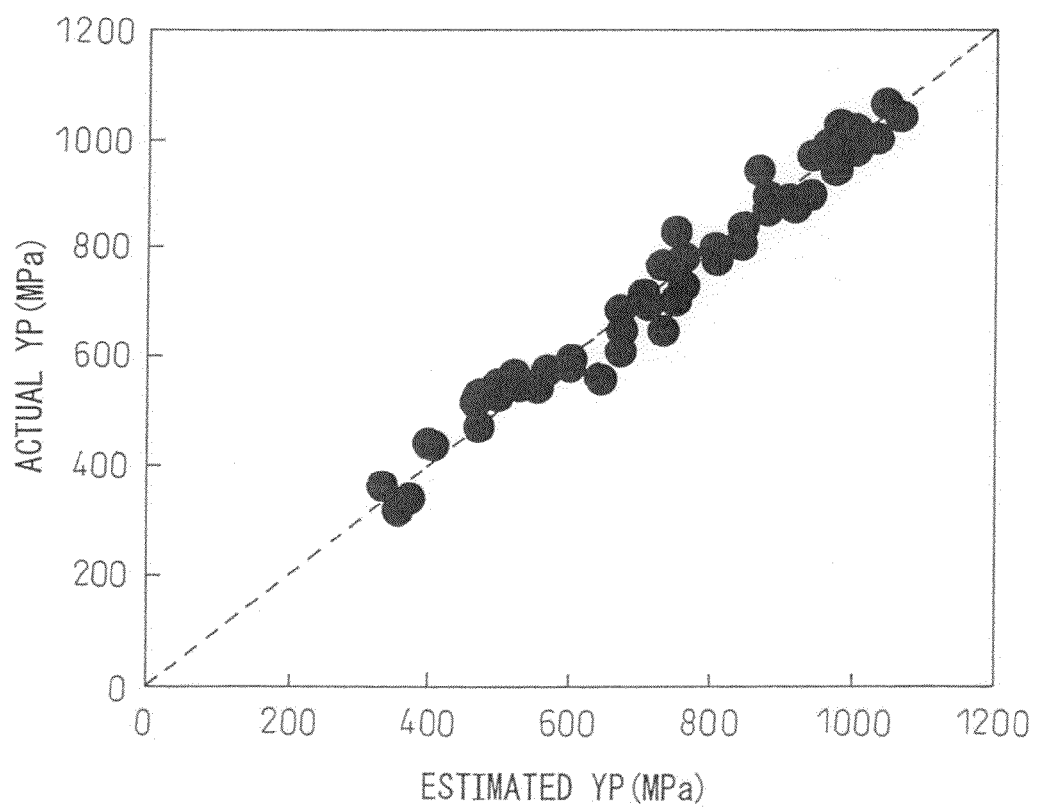
FIG. 6 is a graph showing the correlation between a estimated YP and actual YP.
Figure 7:
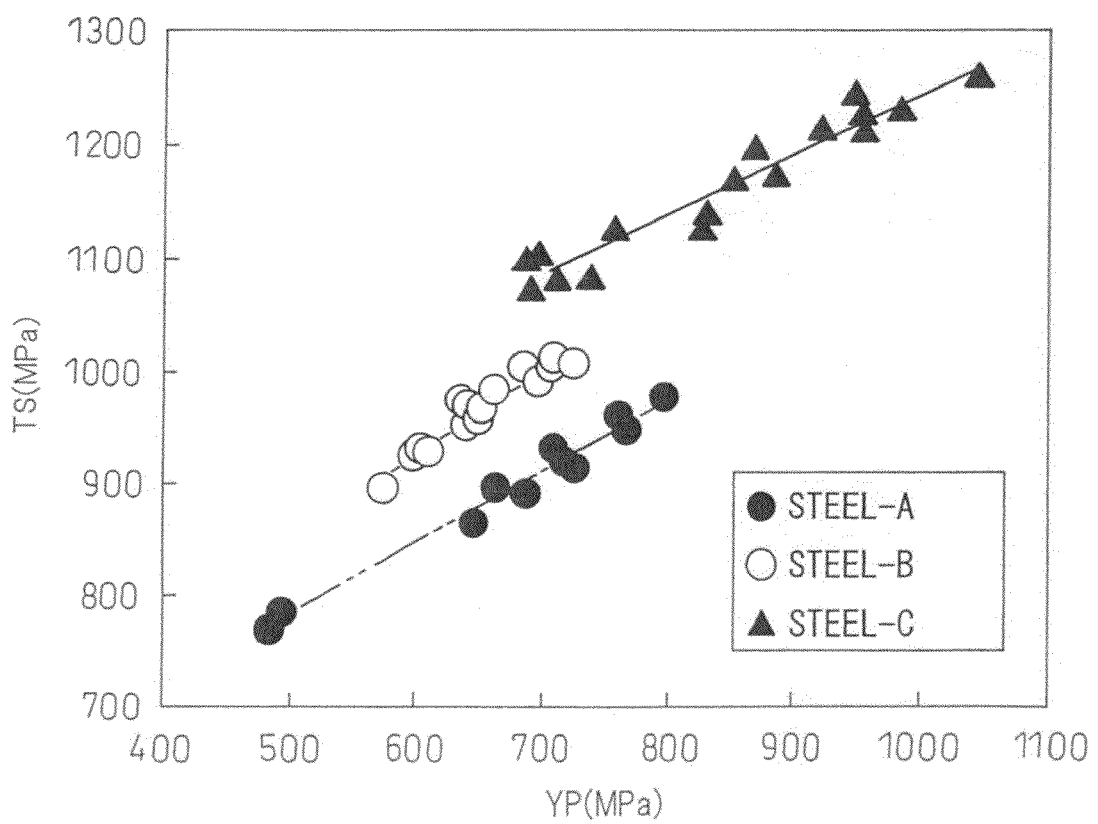
FIG. 7 is a graph showing a relationship between a YP and TS.
Figure 8:
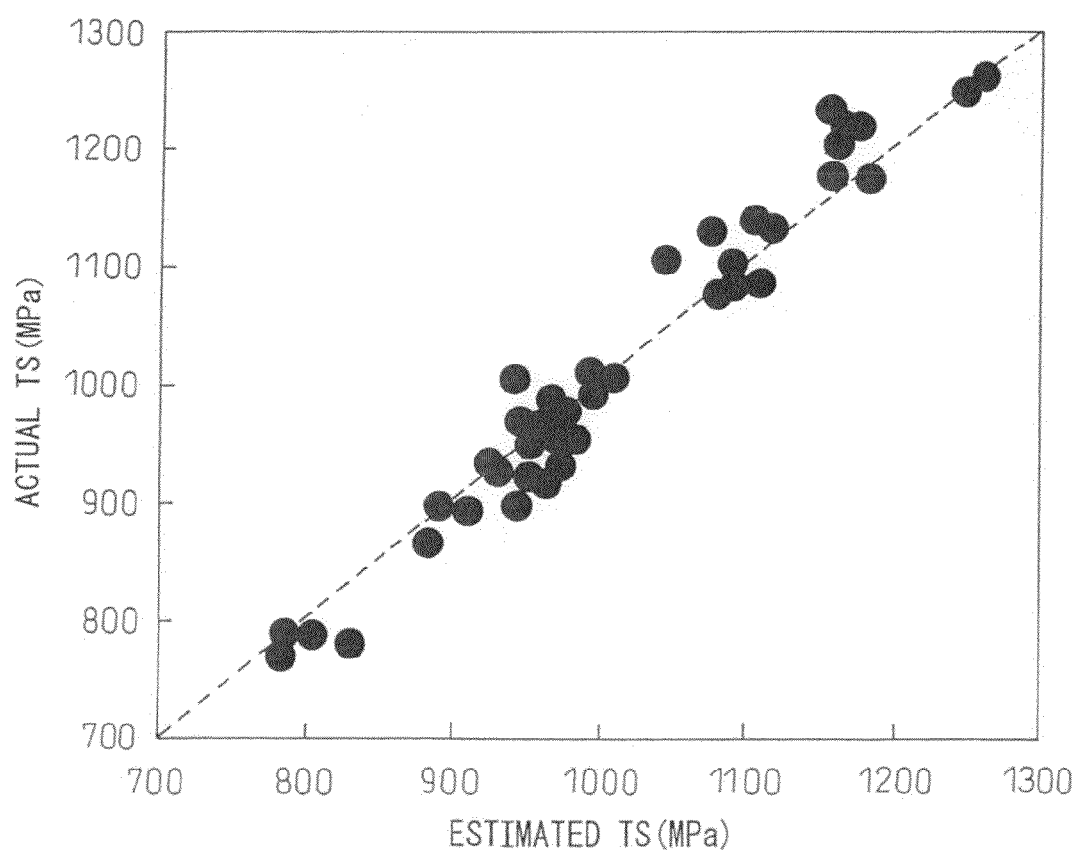
FIG. 8 is a graph showing the correlation between estimated TS and actual TS.

The YP estimated by said mechanical properties estimation formula, as shown in FIG. 6, was confirmed to match the actual YP well (multiple correlation coefficient 0.925). Further, the YP and TS of temper rolled steel sheet have a strong correlation as shown in FIG. 7. The TS is estimated utilizing the relation of TS=e*YP+f shown in this FIG. 7. The relationship with the actual TS is shown in FIG. 8.

In this way, it was confirmed that said mechanical properties estimation formula could be used to accurately estimate the mechanical properties of temper rolled steel sheet. Note that while self evident to a person skilled in the art, the relationship between TS and YP also changes depending on the steel type, so it is also possible to use a formula designed for a specific steel type, for example a higher order formula or a formula using various types of functions. The present invention is not limited to the type of said formula.

Further, even in the case of the above formula, the "e" and "f" in the formula are determined by the characteristics of the line or the steel type and are not particularly limited.

Further, the point that estimating the yield point (YP) is effective for estimating the mechanical properties and the reason for estimating the tensile strength (TS) from the yield point (YP) estimated in this case are explained below.

That is, the yield point (YP) is in the low strain region such as shown by using a 0.2% yield strength as the evaluation value, so even if estimating the yield point (YP) from the usual cold rolling conditions where the reduction rate exceeds 30%, there would be a large gap between the strain region of the yield point (YP) and the strain region actually applied in cold rolling and a problem would arise in the estimation precision.

However, if in the case of the low elongation rate region with an elongation rate of 2.0% or less such as in temper rolling, the strain regions of the yield point (YP) and the actual elongation rate are similar and it becomes possible to estimate the yield point (YP) precisely from the tension, rolling load, and other rolling information.

Figure 9:
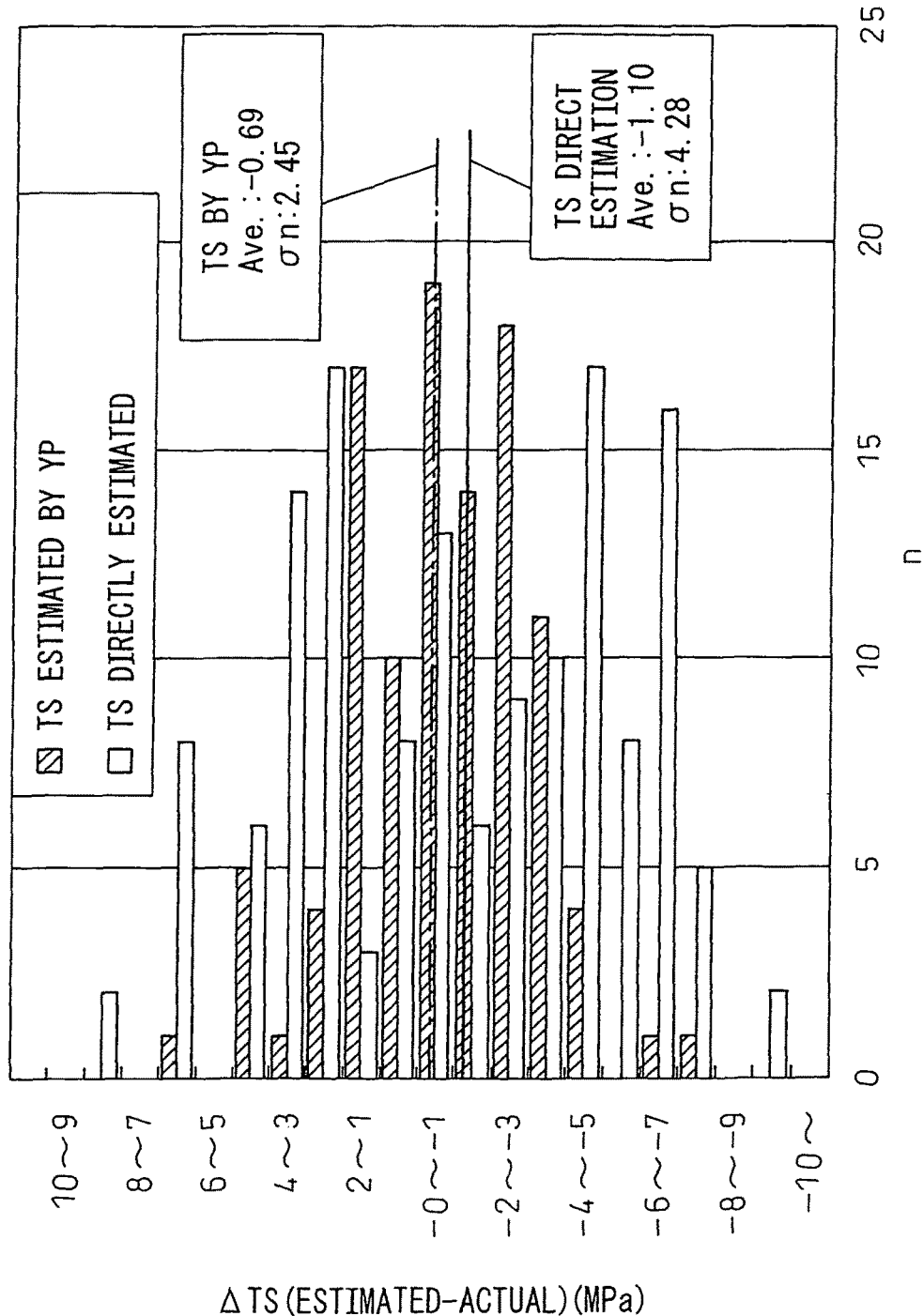
FIG. 9 is a graph comparing a case of directly estimating a TS and the results of estimating a TS from estimation of YP.

On the other hand, in the temper rolled steel sheet covered by the estimation of mechanical properties in the present invention, in general there is tensile strength (TS) in the strain region of about 5 to 25% or so. From this, with estimation of the tensile strength (TS) by an ordinary method such as the tension, rolling load, etc. obtained from the low strain region by 2.0% or less temper rolling, it becomes difficult to directly and precisely estimate the tensile strength (TS) due to the difference in strain regions and the difference in work hardening characteristics dependent on the method of strengthening the steel, the heat treatment method, and other facets of the method of production of the steel sheet. The case of estimating the tensile strength (TS) directly from the temper rolling conditions verified by the inventors and the results of estimation of the tensile strength (TS) from the correlation between the yield point (YP) and the tensile strength (TS) after estimating the yield point (YP) are shown in FIG. 9. From FIG. 9, it will be understood that estimating the tensile strength (TS) from the estimated yield point gives a higher precision than even direct estimation.

Based on these discoveries, the inventors invented the method of not directly estimating the tensile strength (TS) from the temper rolling conditions, but estimating the yield point (YP) from the temper rolling conditions and using a correlative relationship between the yield point (YP) and tensile strength (TS) found in advance to precisely estimate the tensile strength (TS) as well.

In an example of the present invention, the SPM rolling load, SPM tension, and SPM elongation rate continuously sensed at the skinpass mill 2 and the sheet thickness and sheet width continuously sensed at a sheet thickness meter 11 and sheet width meter 12 positioned behind the skinpass mill 2 are input to the process computer 9 shown in FIG. 1 and entered into the YP calculation formula and TS calculation formula of temper rolled steel sheet input to the process computer 9 for calculation to enable the mechanical properties of steel sheet currently being rolled to be grasped in real time.

Note that the values of the sheet thickness and sheet width may also be acquired from a business computer 10 serving as a host computer of the process computer 9.

Further, to improve the precision of the estimation of mechanical properties, it is also possible to use a YP calculation formula and TS calculation formula of temper rolled steel sheet to which at least one of the work roll diameter of said skinpass mill, the friction coefficient between the work roll of the skinpass mill and steel sheet, and the rolling speed of the skinpass mill has been added. The values of the work roll diameter of said skinpass mill and the friction coefficient between the work roll of the skinpass mill and steel sheet may be directly input by the operator into the process computer 9 or input in advance, while the rolling rate of the skinpass mill may be obtained by detecting the rotating speed of the work roll of the skinpass mill or the rotating speed of a not shown bridle roll installed before or after the skinpass mill or other rotating speed inside the skinpass mill or near the same and inputting it into the process computer 9.

Next, an example of how to provide the estimated mechanical property to a user, how to use them, and how to provide feedback to the steel sheet manufacturer is shown in FIG. 10.

Further, as the work performed by a user on the steel sheet, press forming or roll forming is mainly envisioned. FIG. 10 shows the case of press forming by the user.

In the present invention, good precision mechanical properties estimation values of temper rolled steel sheet obtained based on the actual rolling data of the skinpass mill 2 installed at the exit side of the continuous annealing line or galvanization facility 2 are used as the mechanical properties values, so it is possible to provide a user with the mechanical properties characteristic values of any position on the longitudinal direction of the steel sheet or over the entire length. By repeating the estimation of mechanical properties over the entire length referred to here, that is, finely in the long direction, values of mechanical properties estimated at for example 1 m intervals or 10 cm intervals are stored in accordance with the computer capability or demands from the user.

However, when it comes to data for the entire length for each mechanical properties value, the YP data of the entire length or the TS data of the entire length for example, the amount of that data would become enormous. For this reason, it would be preferable to use a computer to store and manage the mechanical properties estimation data and, in accordance with need, compress the data by compression software for provision to the user through a network.

The user of the steel sheet fetches the mechanical properties values obtained through the network server 13 into the computer 14 where it is used for rejecting defective parts on the blanking line 15 of the user. At this time, surface defects and other quality information are also more preferably used to judge and reject defective parts.

Even if not rejecting defective parts, if the user adjusts the press conditions at the press line 16 and if the values of the mechanical properties fluctuate to a pressable extent, if the user of the steel sheet changes the press load, blank holder load, or other press conditions for the pressing in accordance with the values of the mechanical properties obtained through the network, it can minimize the occurrence of scrapped defective parts and perform press operations with a good yield.

The feedback data to the steel sheet manufacturer may in some cases be enormous, so it is preferable that the data be fed back from a computer through a network to the steel sheet manufacturer. More preferably, when a user of the steel sheet removes parts for poor mechanical properties or poor formability, if feeding back information on the mechanical properties conditions of the removed parts and their positions or, when not removing them, but changing the press conditions to deal with the problem, the information on the positions of the steel sheet and information of one or both of the mechanical properties conditions or working conditions of the press line 16 through the network 13 to the steel sheet manufacturer, the steel sheet manufacturer can quickly pinpoint the cause and improve the mechanical properties and thereby can produce and ship out subsequent shipped out steel sheet improved in mechanical properties.

For example, as shown in FIG. 10, rejects at the user, changes of the press conditions, and the mechanical properties values are fed back from the user through the network to the steel sheet manufacturer. The steel sheet manufacturer analyzes this to find the cause, studies countermeasures, and feeds back measures for improvement to the production line. The feedback data may be analyzed by the steel sheet manufacturer for example by downloading it through the network to individual PCs for study or by the business computer 10 or process computer 9 of the steel sheet manufacturer.

The measures for improvement according to the results of analysis are fed back through the business computer or process computer of the steel sheet manufacturer to the steel sheet production line as operating conditions. The steel sheet production line fed back to may be a single line or a plurality of lines.

In this way, according to the present invention, a steel sheet manufacturer and user can share material information of steel sheet to thereby improve the productivity of both sides. In particular, it becomes possible to meet the demands from auto makers for reducing the variation in mechanical properties of high tension materials (high-tensile steel sheet).

INDUSTRIAL APPLICABILITY

According to the present invention, a steel sheet manufacturer can provide a user with detailed material information over the entire length of shipped out steel sheet and a user can use this material information to remove parts of the steel sheet with poor mechanical properties, change the pressing conditions of the steel sheet, or prevent defective products on the production line.

Furthermore, a user can feed back material information on parts removed as poor mechanical properties and information of the relevant positions of the steel sheet to the steel sheet manufacturer.

By having the steel sheet manufacturer and the user share material information of steel sheet, it becomes possible to improve the productivity of the two. The significance of this is extremely great. This contributes to the development of not only the ferrous metal industry producing steel sheet, but also the home appliance industry, automobile industry, construction industry, and other broad industrial fields of the users.

LIST OF REFERENCES

1 continuous annealing line (furnace)
2 skinpass mill
3 heating furnace
4 soaking furnace
5 slow cooling furnace
6 cooling furnace
7 pay-off reel
8 coiling reel
9 process computer
10 host computer (business computer)
11 sheet thickness meter
12 sheet width meter
13 network server
14 user computer
15 blanking line
16 press line

The invention claimed is:

1. A computer-implemented method for estimating and providing material information regarding steel sheet, the method comprising the steps of:
   estimating, by a computer, a yield point of a temper rolled steel sheet by using an estimation formula to calculate the yield point from values of elongation rate, tension, and rolling load for rolling the temper rolled steel sheet in a skinpass mill installed at an exit side of a continuous annealing line or galvanization facility and a sheet thickness and sheet width of the temper rolled steel sheet;
   calculating a tensile strength from the calculated yield point by using a correlation formula which correlates the yield point with the tensile strength; and
   providing the obtained material information including one or both of the yield point and the tensile strength to a user of said steel sheet through a computer and network.

2. A computer-implemented method for providing material information regarding steel sheet as set forth in claim 1, further comprising the step of:
   measuring the values of elongation rate, tension, and rolling load for rolling the temper steel sheet in the skinpass mill and the sheet thickness and sheet width of said steel sheet.

3. A computer-implemented method for providing material information regarding steel sheet as set forth in claim 1, further comprising the step of:
   continuously measuring said values of elongation rate, tension, and rolling load of for rolling the temper steel sheet and the sheet thickness and sheet width of said steel sheet over the entire length of said steel sheet, using these values to estimate the mechanical properties of temper rolled steel sheet.

4. A computer-implemented method for utilizing material information regarding steel sheet, comprising the step of:
   removing a defective part of the steel sheet by using the material information provided by a method as set forth in claim 1.

5. A computer-implemented method for utilizing material information regarding steel sheet as set forth in claim 4, further comprising the step of:
   feeding back by the user the material information and positioning information of the removed part of the steel sheet and one or both of the material information and press forming conditions of the remaining part of the steel sheet to the manufacturer of said steel sheet through a computer and network.

6. A computer-implemented method for utilizing material information regarding steel sheet, comprising the step of:
   changing press forming conditions of the steel sheet by using the material information provided by a method as set forth in claim 1.

7. A computer-implemented method for utilizing material information regarding steel sheet as set forth in claim 6, further comprising the step of:
   feeding back by the user the material information and positioning information of the steel sheet and the changed press forming conditions of the steel sheet to the manufacturer of said steel sheet through a computer and network.

8. The computer-implemented method for providing material information regarding steel sheet as set forth in claim 1, wherein the estimation formula is the following equation:

$$YP = a*\text{elongation rate (\%)} + b*\text{tension (MPa)} + c*[\text{sheet thickness (mm) of steel sheet} * \text{linear load (ton/m)}] + d,$$

wherein YP is the yield point, wherein the linear load is the rolling load divided by the width of the steel sheet, and wherein a, b, c, and d are parameters determined by characteristics of steel sheet production line and strength of the steel sheet.

9. The computer-implemented method for providing material information regarding steel sheet as set forth in claim 8, wherein the correlation formula is the following equation:

$$TS = e*YP + f,$$

wherein TS is the tensile strength, and wherein e and f are parameters determined by characteristics of steel sheet production line or steel type.

* * * * *